United States Patent
Vassarotti et al.

(10) Patent No.: US 6,312,591 B1
(45) Date of Patent: *Nov. 6, 2001

(54) FILTRATION CELL FOR TANGENTIAL FLOW FILTRATION AND FILTRATION SYSTEM MAKING USE OF SUCH CELL

(75) Inventors: Vincenzo Vassarotti, Bugnaux sur Rolle (CH); Colin Lanyi, Minchinhampton; Christopher Biddell, Stonehouse, both of (GB)

(73) Assignee: Sartorius AG, Gottingen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/150,790

(22) Filed: Sep. 10, 1998

(30) Foreign Application Priority Data

Sep. 10, 1997 (SE) .................................................. 9703302

(51) Int. Cl.[7] .................................................. B01D 61/20
(52) U.S. Cl. .................................. 210/195.2; 210/321.75; 210/321.84; 210/490; 422/191; 73/863.23
(58) Field of Search .............................. 210/195.2, 257.2, 210/321.75, 321.84, 456, 194, 321.65, 416.1, 490; 422/101; 436/178, 180; 73/64.56, 863.23

(56) References Cited

U.S. PATENT DOCUMENTS

| | | | |
|---|---|---|---|
| 2,364,366 | * 12/1944 | Jahreis et al. | 210/321.84 |
| 3,608,610 | * 9/1971 | Greatorex et al. | 210/321.84 |
| 5,194,154 | 3/1993 | Moyer et al. | 210/510.1 |
| 5,228,991 | 7/1993 | Strohm et al. | 210/321.8 |
| 5,282,972 | * 2/1994 | Hanna et al. | 210/321.84 |
| 5,601,727 | * 2/1997 | Bormann et al. | 210/194 |
| 5,660,728 | * 8/1997 | Saaski et al. | 210/321.84 |

FOREIGN PATENT DOCUMENTS

| | | |
|---|---|---|
| 120264 | 10/1984 | (EP) . |
| 9421362 | 9/1994 | (WO) . |
| 9700121 | 1/1997 | (WO) . |
| 9704857 | 2/1997 | (WO) . |

* cited by examiner

Primary Examiner—Joseph W. Drodge
(74) Attorney, Agent, or Firm—Young & Thompson

(57) ABSTRACT

A filtration cell for carrying out a tangential flow filtration of a sample liquid contains at least two blocks and at least two filtration elements arranged between each pair of two adjacent blocks. The filtration elements each include an outlet for filtrate, a sheet of support material and two generally flat ultrafiltration or microfiltration membranes, arranged on either side of the support material in a sandwich construction. Each of the blocks, at a side adjacent the membranes, is provided with a respective channel for feeding a flow of sample liquid tangentially over the membranes such that each channel is connected in parallel with the inlet for the flow of sample liquid to be filtered and with an outlet for a concentrated solution. Each channel includes in its longitudinal direction a number of subsequent channel sections separated by transitional zones and is constructed and arranged such that the main flow direction in subsequent sections changes abruptly in the transitional zones.

5 Claims, 7 Drawing Sheets

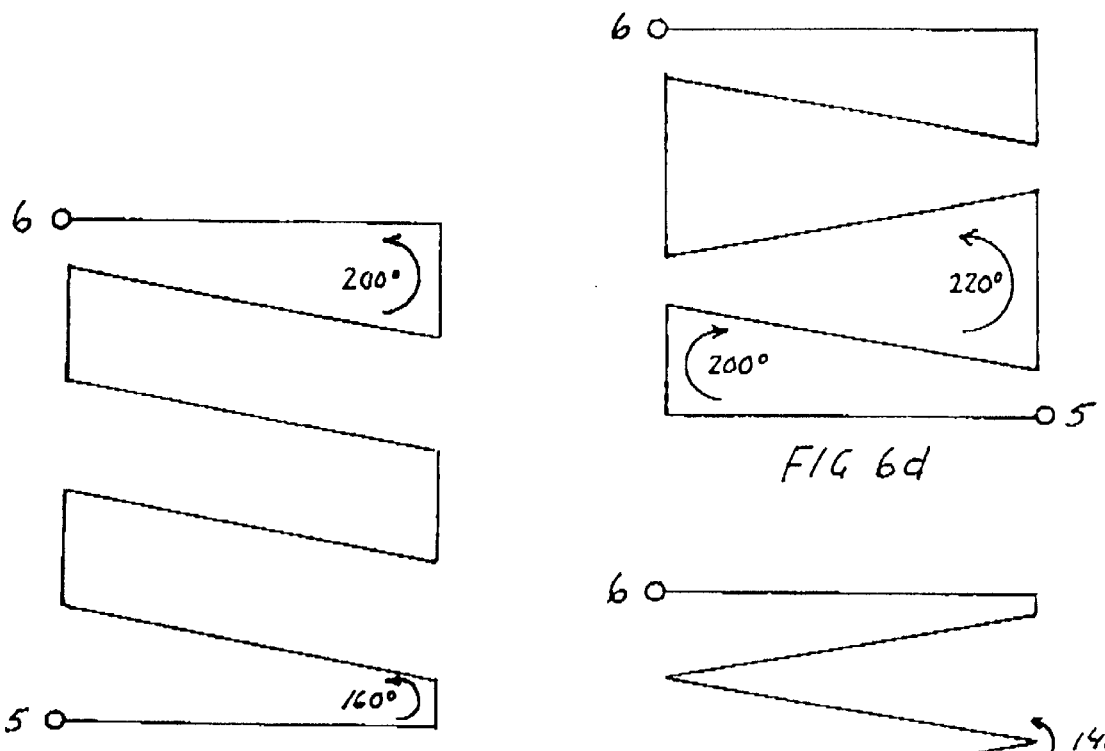
FIG 6d
FIG 6a
FIG 6c
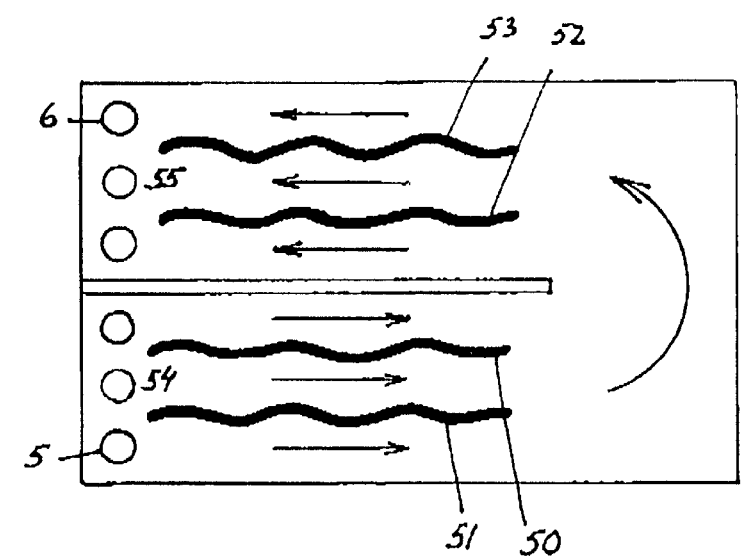
FIG 9

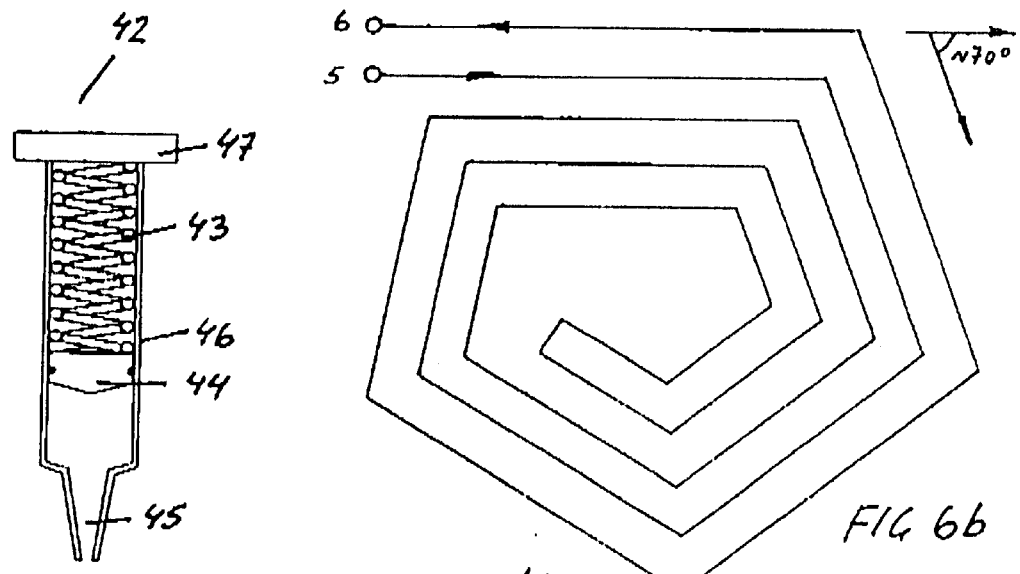
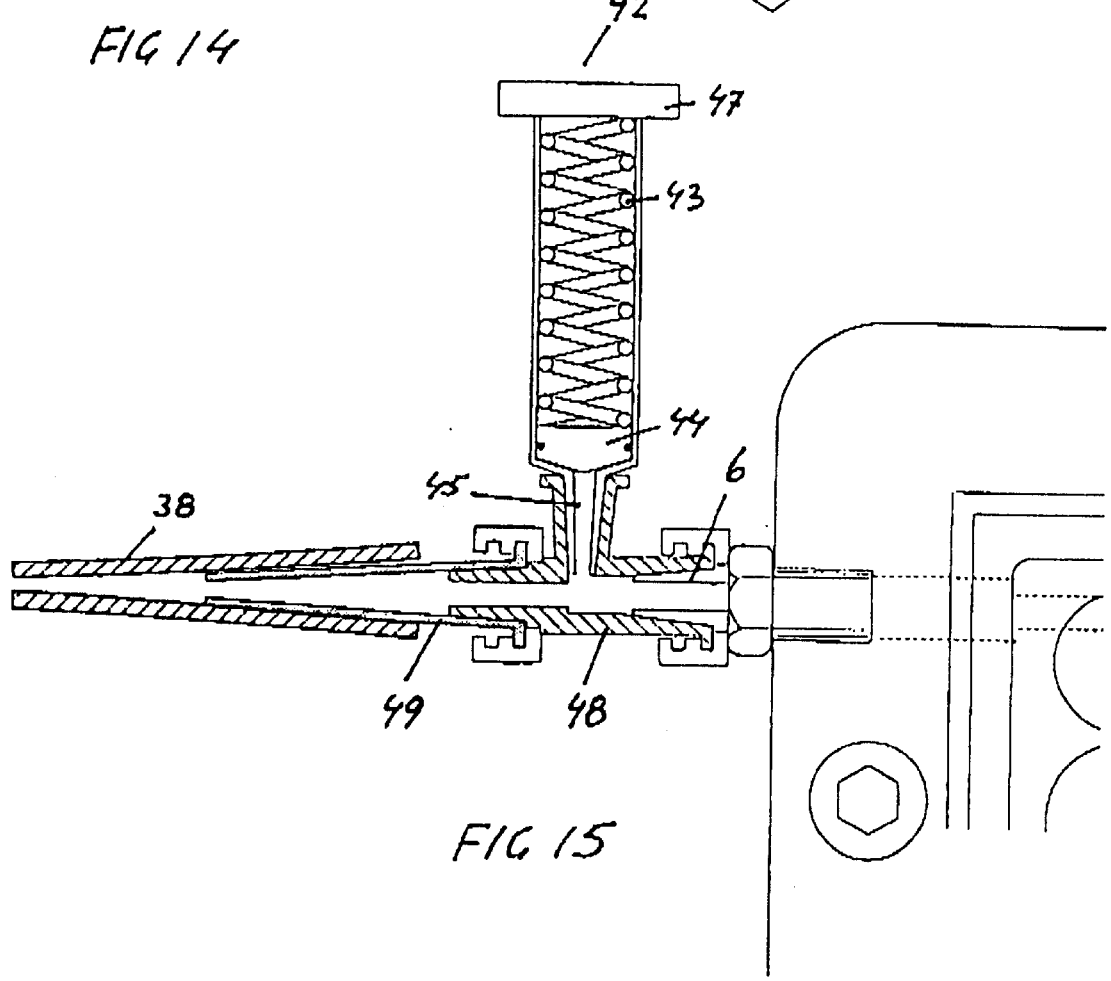

FILTRATION CELL FOR TANGENTIAL FLOW FILTRATION AND FILTRATION SYSTEM MAKING USE OF SUCH CELL

TECHNICAL FIELD

This invention relates to tangential (cross) flow filtration cells employing flat membranes which can be used on a laboratory scale e.g. for concentrating and or fractionating macromolecules in a solution.

In a filtration system the filtration cell is connected to a pump that typically draws liquid from a sample reservoir through the cell and recirculates sample liquid through a loop including the cell. The necessary system pressure is created by a flow restrictor positioned at the outlet of the cell and the pressure is monitored by a pressure gauge. Due to the pressure difference between the feed side and the permeate side of the membrane filtrate is permeating through the filter and is collected outside the cell.

The cell and the system could also easily be scaled up to be used on an industrial scale for filtering and clarifying liquids like e.g. fruit juices by ultrafiltration or microfiltration.

BACKGROUND ART

Many industrial, food and biotechnology companies use micro- and ultrafiltration equipment and methods in the processing of solutions. As examples, filtration is used as a sterilising step to remove bacteria, as a clarification step to remove suspended solids and contaminants, as a concentration step for proteins and other macromolecules or as a purification step to eliminate unwanted micro-molecules such as salts. Alternative membranes and porosities are used to suit specific applications and process requirements.

Especially for larger volumes the so called crossflow or tangential flow technique is used.

Filter elements for this type of filtration in the form of membranes (e.g. of the spiral wound, hollow fibre or flat type) are mounted in pressure resistant housing to form filtration modules or cells. In a filtration system including such cells a pump is used to feed the solution to be filtered through the cell tangentially across the membrane surface. The speed of solute filtration is governed by a number of parameters like general membrane characteristics and porosity, pressure and the level of fouling that occurs on the membrane surface.

Problems related to gel polarisation or fouling of the membrane which greatly reduces the speed of filtration have been major handicaps in the development of ultrafiltration techniques. These problems are caused by several factors, the most important of which are the formation of a gel layer and the accumulation of retained particles on the membrane surface which results in a partial blockage of the membrane pores during solute filtration. The phenomenon frequently results in a tenfold or greater reduction in membrane hydraulic permeability when compared to the original pure water permeation rate. The ultimate impact of these problems is the need for significantly increased operating pressure and membrane area requirements for a given filtration capacity, increasing hold up losses in the system i.e. losses of concentrated sample which can not be drained from the cell, adding cost and finally making filtration less competitive than alternative processing techniques.

Important parameters that also need to be taken into account in the design of filtration cells include minimising liquid hold up volume per membrane unit area, a low pressure drop across the length of the flow path, ease of cleaning with minimum dead spaces, ability to fully drain the cell, ease of scaling up or down to large capacity or small pilot systems, minimum energy requirement which means high flow rate in combination with low pressure drop across the cell and overall economy.

The use of high flow, long, thin channel configurations using either membranes in the form of a flat plate or hollow fibre bundles have shown improvements in reducing fouling whilst achieving low hold up and energy requirements.

The present invention is directed to a cells and systems making use of flat membranes.

In a known filtration cell a flat, thin channel is arranged in a spiral configuration on one side of a circular membrane. Filtrate outlet and inlet ports are fitted at the centre and the outer edge of the cell respectively. The outlet port at the centre is arranged perpendicular to the flat channel and the membrane.

The major problems associated with this configuration, is the poor utilisation of available membrane area when cutting the membrane (circular) which of course increases the cost of the membrane. Additionally this type of cell is not suitable when scaling up to large size process systems due to the central outlet which does not allow the stacking of multiple cells. For these reasons this type of configuration has been mostly limited to small laboratory systems.

Another known filtration cell using membranes of the flat type is sold by the company MILLIPORE under the trademark MINITAN. This cell has an essentially rectangular membrane which is swept by sample solution flowing through multiple straight parallel channels from an inlet manifold at one edge of the filter membrane to an outlet manifold at an opposite edge of the filter membrane.

Another problem with existing tangential flow cells relates to the need to control back pressure at the cell recirculation outlet in conjunction with pump speed setting in order to create suitable transmembrane pressure within the cell itself.

In existing systems, a valve is used to restrict flow whilst pump speed is also varied until adequate pressure is achieved. In small laboratory systems a so called pinch valve is typically used to compress the outlet tube whilst larger process systems use more sophisticated mechanical valves. The pinch valve is inexpensive but is difficult to accurately control whilst mechanical valves are more precise but add a significant cost to the overall process. In both cases, the interdependency between valve and pump setting makes process control complicated and time consuming.

To achieve adequate pressure control, at least one pressure gauge must also be fitted to the filtration system, usually at the inlet or outlet of the filtration cell. Diaphragm valves which are frequently used for this purpose result in a large liquid dead volume entering the internal mechanism which is difficult to drain with negative consequences particularly when sanitary operation is essential. Sanitary designs that have been developed to reduce this problem are expensive and cannot normally be justified in a small laboratory system. In addition, due to the pulsation effect produced by most pumps, pressure readings fluctuate at a high frequency making visual control difficult and inaccurate.

In addition to minimising hold up volume in the filtration cell itself, it is just as important many times to reduce volume and surface area in the recirculation loop including the feed reservoir, pump and connective tubing, so as to allow a high level of final concentration and/or maximum filtrate volume. As initial volumes are frequently large, the feed or sample reservoir must usually be placed at a significant distance from the cell and pump assembly. This requires additional tubing for recirculation which adds to the hold up volume and it is difficult to pump liquid completely from a large reservoir so that not all the initial sample can always be processed.

When e.g. processing small volumes of sample liquid and the retentate has a high value it is clearly of interest to keep the hold up volume of the cell as well as the complete recirculation loop at a strict minimum. Many times you have this situation when processing samples in a laboratory. On the other hand when the processed product is the filtrate and the value lost in the hold up volume is of less importance, e.g. when clarifying fruit juices, the actual hold up volume is not critical.

BRIEF DESCRIPTION OF THE INVENTION

One object of this invention is to provide a tangential flow filtration cell that achieves a high level of cross-flow turbulence in order to reduce problems related to gel polarisation and fouling of the membrane surface.

It is another object of this invention to provide a tangential flow filtration cell that has a square, rectangular or trapezoidal shape in order to maximise yield from rolls or sheets of membrane material when cutting the membrane.

It is another object of this invention to provide a tangential flow filtration cell which can be expanded by stacking consecutive filter cells in series and only requiring pressure plates at each end of the complete assembly.

It is another object of this invention to provide a tangential flow filtration cell where the inlet and outlet ports are mounted on the same face of the housing thereby reducing the overall length of the recirculation tubing.

It is another object of this invention to provide a tangential flow filtration cell which has low liquid hold-up per unit filter area.

It is another object of this invention to provide a tangential flow filtration cell which requires a low level of energy for operation.

It is another object of this invention to provide a tangential flow filtration cell whose flow channel height can be varied to accommodate the flow requirements of solutes of differing content and viscosity.

It is another object of this invention to provide a tangential flow filtration cell whose flow channel length can be chosen to accommodate the flow requirements of solutes of differing content and viscosity It is another object of this invention to provide a tangential flow filtration cell whose flow channel width can be chosen to accommodate the flow requirements of alternative sample volumes.

It is another object of this invention to provide a tangential flow filtration cell whose flow channel width can be chosen to decrease progressively along its length to maintain cross flow velocity as solvent progressively passes through the membrane.

It is another object of this invention to provide a tangential flow filtration cell whose flow channel height can be chosen to increase progressively along its length to reduce drag and related pressure drop as liquid progresses along the channel.

It is another object of this invention to provide a tangential flow filtration cell whose flow channel width can be chosen progressively increasing along its length to reduce drag and related pressure drop as liquid progresses along the channel.

It is another object of this invention to provide a tangential flow filtration cell whose flow channel width can be chosen progressively decreasing along its length to maintain cross flow velocity as solvent progressively passes through the membrane.

It is another object of this invention to provide a tangential flow filtration cell whose flow channel is essentially free of dead spaces which are not readily wetted during solute recirculation.

It is another object of this invention to provide a means of regulating flow pressure on tangential flow filtration cells without the need for back pressure valve adjustment.

It is another object of this invention to provide a filtration system with a low cost pressure gauge that drains completely when liquid pressure is released.

It is another object of this invention to provide a low cost pressure gauge that is dampened when subjected to the pressure pulsation of liquid pumps.

It is another object of this invention to provide a tangential flow recirculation system with reduced liquid volume and surface area in the recirculation loop.

It is another of this invention to provide a tangential flow recirculation loop with reduced liquid hold up volume and surface area.

It is another of this invention to provide a tangential flow recirculation loop that is easy to drain completely.

It is another object of this invention to provide a tangential flow recirculation loop that allows periodic bleeding of concentrated solution.

It is another object of this invention to provide a tangential flow recirculation loop that can be used for both molecular concentration and washing.

BRIEF DESCRIPTION OF THE DRAWINGS

Further objects, uses and advantages with the invention will be apparent from the reading of this description which proceeds with reference to the accompanying drawings forming part thereof and wherein:

FIGS. 6a–d shows examples of flowpaths for different combinations of switching angles between subsequent channel sections, FIG. 9 shows the arrangement of a channel having two sections provided with turbulence increasing means, FIG. 14 shows a new design of a pressure gauge, FIG. 15 shows a pressure gauge and a flow restrictor mounted on a filtration cell according to the invention,

DESCRIPTION OF THE PREFERRED EMBODIMENTS

Figure 2:
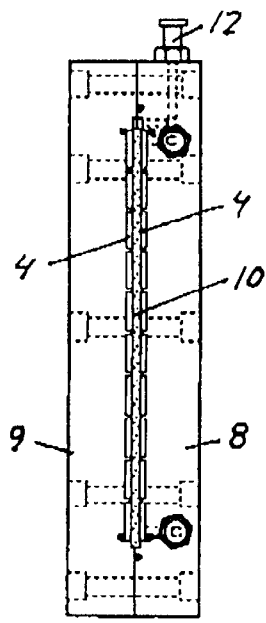
FIG. 2 shows a sectional view of the cell according to FIG. 1.
Figure 1:
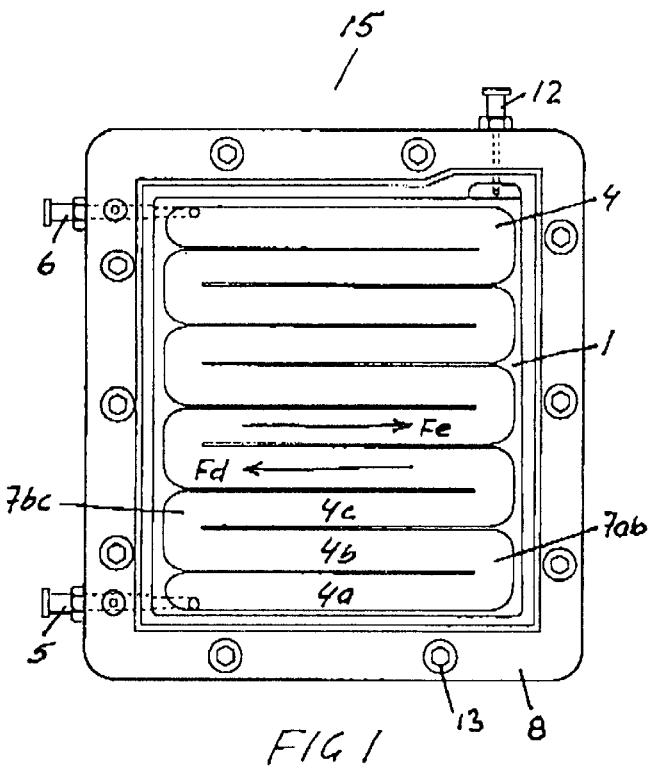
FIG. 1 shows a filtration cell according to the invention.

FIG. 1 shows an embodiment of a filtration cell with the general designation 15 according to the invention. This cell has two thin tangential flow channels 4 arranged on either side of a filtration element 10. The filtration element comprises two filtration membranes 1, e.g. of microfiltration or ultrafiltration type, arranged on either side of a sheet of sintered porous material in sandwich construction. Other configurations could be envisaged. A more basic embodiment could for instance comprise only one flow channel 4 and one membrane 1. The porous material could be replaced with a generally flat plate having a rough or channelled surface allowing for the filtrate to escape along the surface to an outlet port 12 for filtrate. The membranes mounted on the porous material define a feed side 2 being swept by the sample solution and a permeate side 3 in contact with the porous support material, cf. FIG. 3.

A pressure resistant housing comprising two blocks 8, 9 of preferably transparent plastic material tightly fixed to each other by means of bolts constitutes the body of the cell. The flow channels could be machined into the inner opposite surfaces of the blocks 8, 9. In a double channel configuration like the one shown in FIG. 1 the channels could be mirrored but they do not have to be. The blocks including the channels could of course also be moulded in plastic or any other suitable material. Finally the parts of the block including the channels and the inlet and outlet ports could be moulded separately and could be mounted in an appropriate combination together with filter elements, gaskets and other necessary parts between external pressure plates which could then be completely flat.

An inlet and an outlet 5, 6 for sample solution are arranged in the housing communicating through inlet and outlet channels 16 with the two filtration channels 4 which in this embodiment are arranged in parallel.

Figure 3:
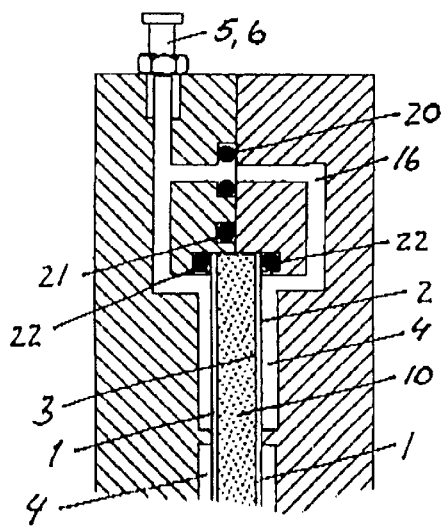
FIG. 3 shows a detail of the inlet and outlet configurations for the sample solution with examples of gaskets in the form of O-rings.

In order to make the cell liquid tight and separate the sample solution from the filtrate a certain number of gaskets has to be arranged. This can of course be made in different ways. In FIG. 3 one way to arrange these gaskets is illustrated. A small O-ring 20 is sealing off the input/output channel 16 at the surface between the two blocks 8 and 9. The diameter of this O-ring is only somewhat bigger than the diameter of the channel. An external gasket, in the form of a larger O-ring 21 is arranged in a groove which reaches all around the internal part of the cell and is sealing the internal part of the cell from the environment. This gasket is shown more in detail in FIG. 5. Additionally one O-ring 22 on each side of the filter element 10 is in this embodiment used for protecting the filtrate from mixing with the sample/concentrate solution. This gasket can also be seen in FIG. 5.

Figure 5:
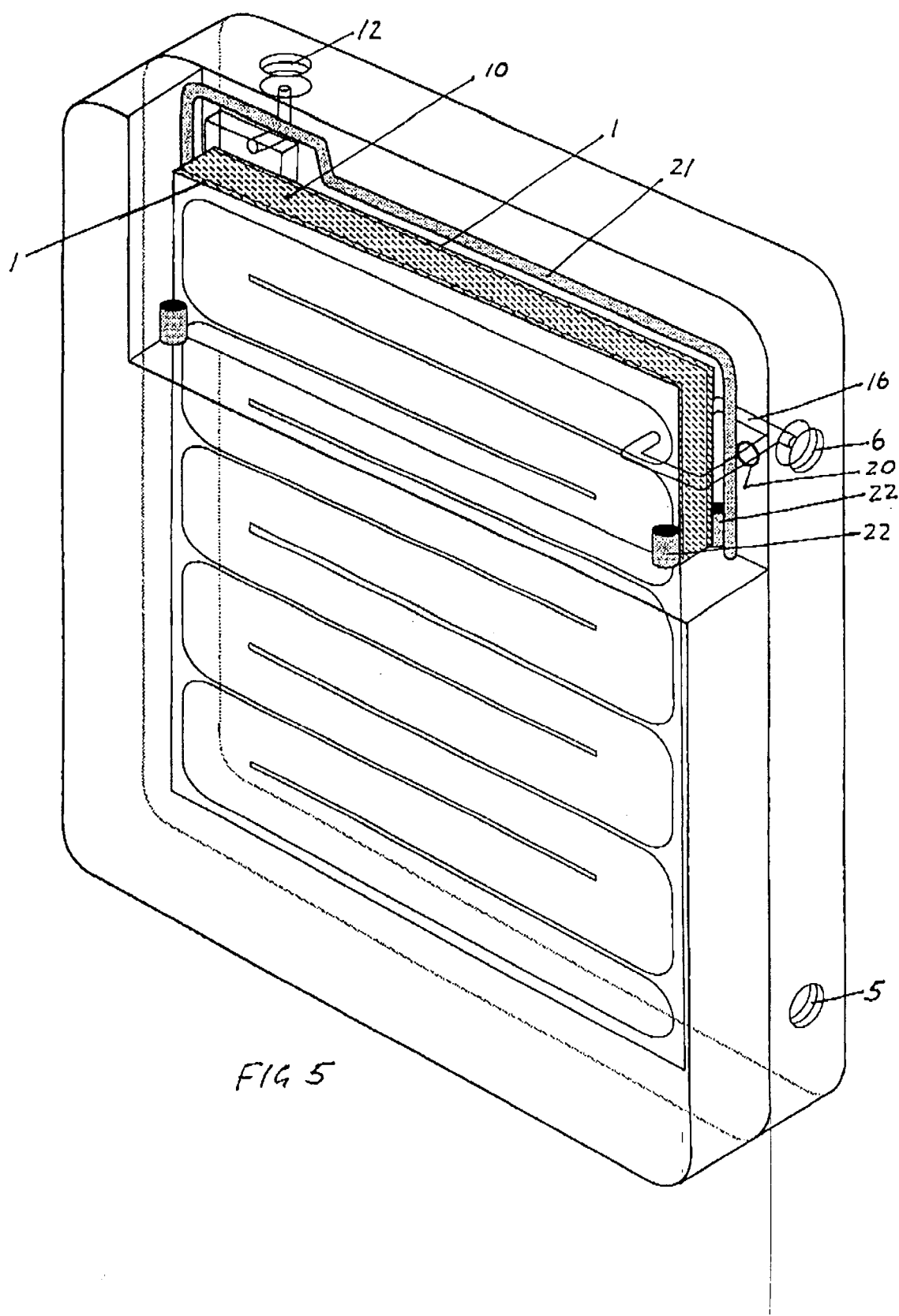
FIG. 5 shows in larger scale a filtration cell according to the invention with the arrangement of two filter membranes in a sandwich construction.

In FIG. 5 the arrangement of the two filter membranes 1 on either side of the porous sintered material in the form of a generally flat plate is shown in a perspective view. One of the two thin tangential flow channels 4 in contact with the feed side of one of the membranes is also illustrated. The outlet 6 for the sample flow is connected to the endportion of the two channels 4 in parallel via the inlet/outlet channels 16 as also shown in FIG. 3. The inlet 5 is connected to the other endportions of the two flow channels in the same way.

From the inlet to the outlet the channel 4 comprises in its longitudinal flow direction a number of subsequent channel sections 4a, 4b, 4c etc. (cf. FIG. 1) separated by transitional zones 7ab, 7bc, 7cd etc.. Each channel section is associated with a main flow direction Fa, Fb, Fc etc. (cf. FIG. 1).

The channel sections 4a, 4b, 4c etc. are so arranged in this embodiment of the invention that the main flow direction Fa, Fb, Fc etc. In subsequent channel sections is changing 180° when the flow is passing the transitional zones 7ab, 7bc, 7cd etc. between subsequent sections. This gives the thin channel a meander form forcing the flow of sample solution back and forth over the surface of the filter in a plane parallel to the filter surface which on one hand efficiently makes use of the available filter surface and on the other hand creates turbulence which has a very efficient self cleaning effect on the filter surface. For a broad range of flowrates and liquids of different viscosity the problem of fouling is practically eliminated. The flux rate, i.e. the flow of filtrate through the membrane (measured in e.g. ml/min) per square unit of membrane has been possible to raise considerably in relation to known devices by means of this new design for the filter cell.

A rectangular form of the membrane of course give better yield than other geometrical forms like round, oval etc. when cutting the membrane out from a larger piece of flat membrane. On top of this the surface of the rectangular membrane in this embodiment is used to an optimum.

The sudden sharp turns (the transitional zones represent very short flowpaths in relation to the length of the channel) create turbulence. However, the change in the main flow direction between subsequent channel sections does not have to be 180°, to reach this effect and can even vary within one and the same cell.

FIGS. 6a–d show a few different examples of configurations of flowpaths realised with different combinations of switching angles between subsequent channel sections. The subsequent flow channel sections are in these figures represented by straight lines in the direction of the associated main flow direction.

In FIG. 6a the direction changes about 160° in the first transitional zone and about 200° in the last transitional zone. Between intermediate zones the direction changes 180°.

FIG. 6b shows an embodiment having a double spiral configuration achieved by successive changes of the directions of the main flow by about 70° in each transitional zone.

FIG. 6c shows an embodiment in which the first and last switches are about 160° and the intermediate switches about 140°.

The embodiment according to FIG. 6d has switches between 200 and 220°.

Of course many other configurations could be envisaged with other switching angles. Certain embodiments have especially low pressure drop over the cell, others have an especially efficient utilisation of the available membrane surface. The variant according to FIG. 6c used in vertical position is especially easy to drain which is of importance both when it comes to emptying the system of valuable concentrate and when it comes to cleaning the cell.

Excellent results have been achieved with switching angles between around 45° and up to around 240° which angles are not limiting the possible interval for the invention.

Figure 7:
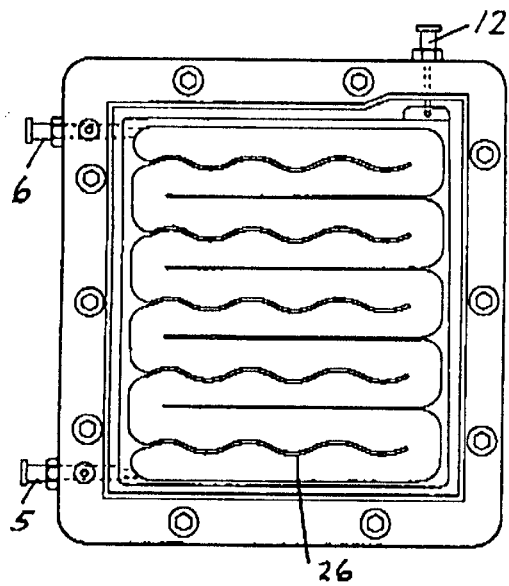
FIG. 7 shows another embodiment of the filtration cell according to the invention with one filtration channel.
Figure 8:
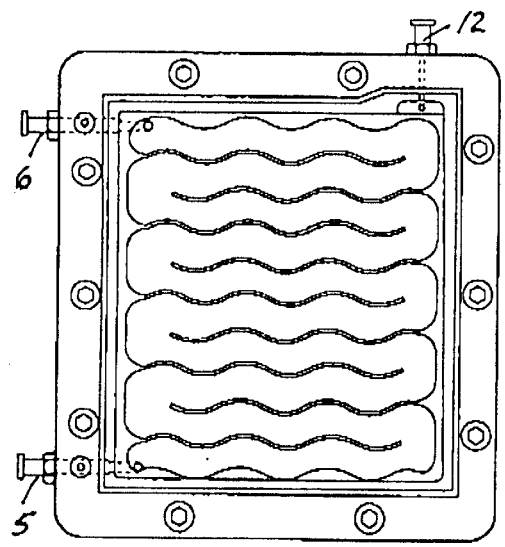
FIG. 8 shows a further embodiment of the filtration cell according to the invention with one filtration channel.

The FIGS. 7 and 8 show a cell of the type already discussed in connection with FIGS. 1 to 5 in which at least one sidewall in each channel section has been given an undulating form. This will further create, increase and/or maintain the turbulence in the flow.

If we assume that the thickness of the channel, i.e. the dimension perpendicular to the plane of the paper (and the membrane), is constant over the length of the channel, the embodiment according to FIG. 7 will have a periodically changing cross sectional area of the channel.

The embodiment according to FIG. 8 on the other hand will have a more or less constant cross sectional area along the channel with the same assumption.

Figure 4:
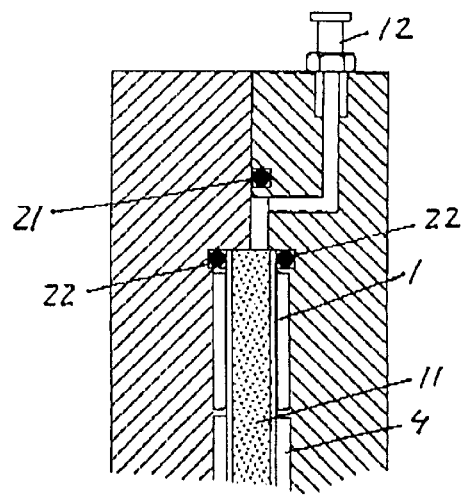
FIG. 4 shows a detail of the outlet configuration for the filtrate.

To further increase the turbulence in the channel the sidewall 25, cf. FIG. 4, of the channel which is opposite to the membrane can be given a profiled form. In the embodiment of FIG. 7 the constant cross sectional area could e.g. be restored at the same time as a movement of the liquid perpendicular to the membrane surface is introduced by giving the sidewall 25 a waveform phase shifted 180° in relation to the waveform of the sidewall 26 of FIG. 7, i.e. in a position along the channel where one waveform has a maximum the other has a minimum. To reach other effects on the cross sectional area along the channel, e.g. a steadily increasing or decreasing cross section it would of course be possible to give the sidewalls, especially sidewall 25, an appropriate form.

As described above the flow channel and the corresponding inlet and outlet ports could be moulded separately in one piece. Such a piece or such pieces could be mounted in an appropriate combination together with filter elements, gaskets and other necessary parts between external pressure plates which could then be completely flat to form a single cell or a stacked configuration of cells. It is evident that a setup of differently configured flow channel elements could be provided so that the user himself could put together a cell according to his special requirements.

It is easily understood that by profiling the sidewall 25 (and the sidewalls 26) in an appropriate way it would even be possible to give the sample flow a spiral type of movement inside the channel which very efficiently would sweep the membrane surface. The cleaning effect is dependent on the flow rate in the channel. By designing the channel appropriately it is even possible to reach resonance conditions for certain flow rates.

FIG. 9 shows the arrangement of a channel having two sections with the switching angle between the sections being 180°. Each channel section is by means of two (could be one or several) partition walls 50, 51, 52, 53 separated into three (two or several) parallel sub-sections. The partition walls have a waveform which creates and/or maintains turbulence. The partition of the flow between the sub-sections and the collection of the flow from the sub-sections is taking place in an inlet and an outlet manifold zone 54, 55 respectively.

Figure 10:
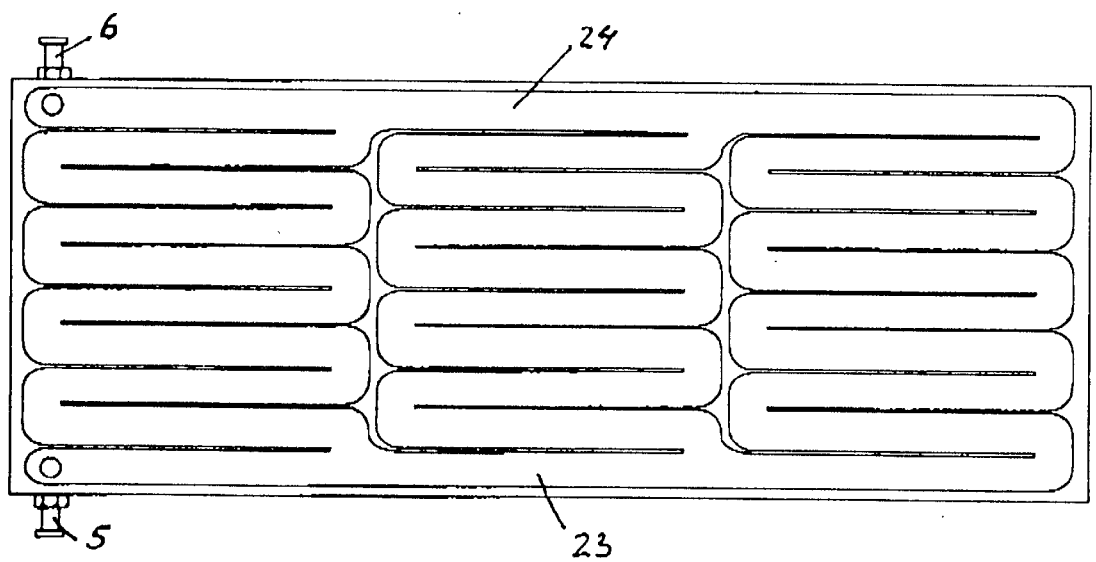
FIG. 10 shows a filtration cell configuration having three channels in parallel.

Several flow channels of the type described above could be arranged in parallel over the surface of one and the same membrane within a single cell. Such a configuration including three channels in parallel is shown in FIG. 10. in order to partition the flow between the channels inlet 23 and outlet 24 manifolds are integrated in the cell. The cross sectional area of the inlet and outlet manifolds does not have to be constant over the length. In a specific embodiment, however, it is constant and large enough to evenly distribute the flow over the different channels.

Figure 11:
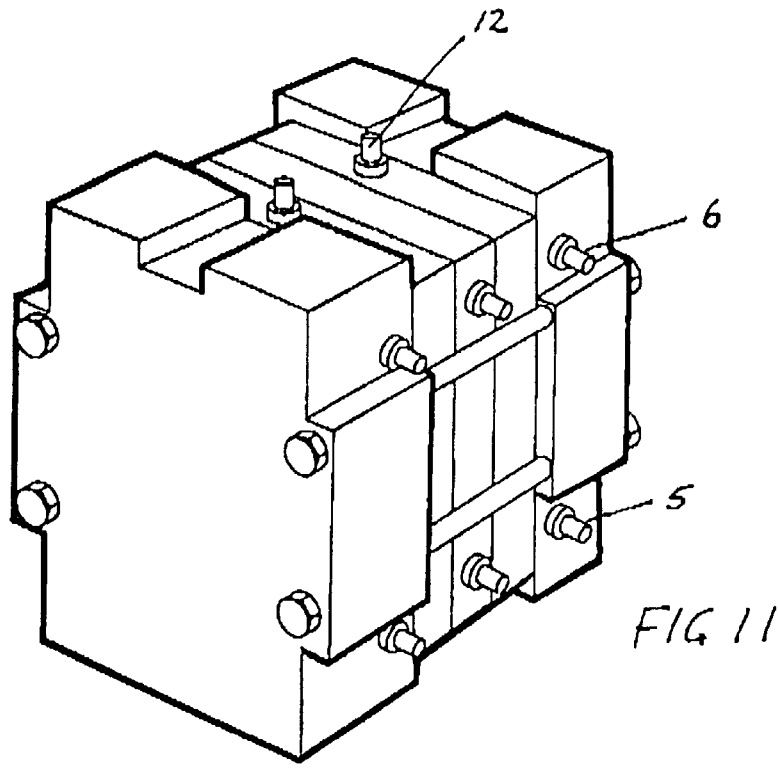
FIG. 11 shows two filtration cells each provided with a double filter stacked together between to endplates.
Figure 12:
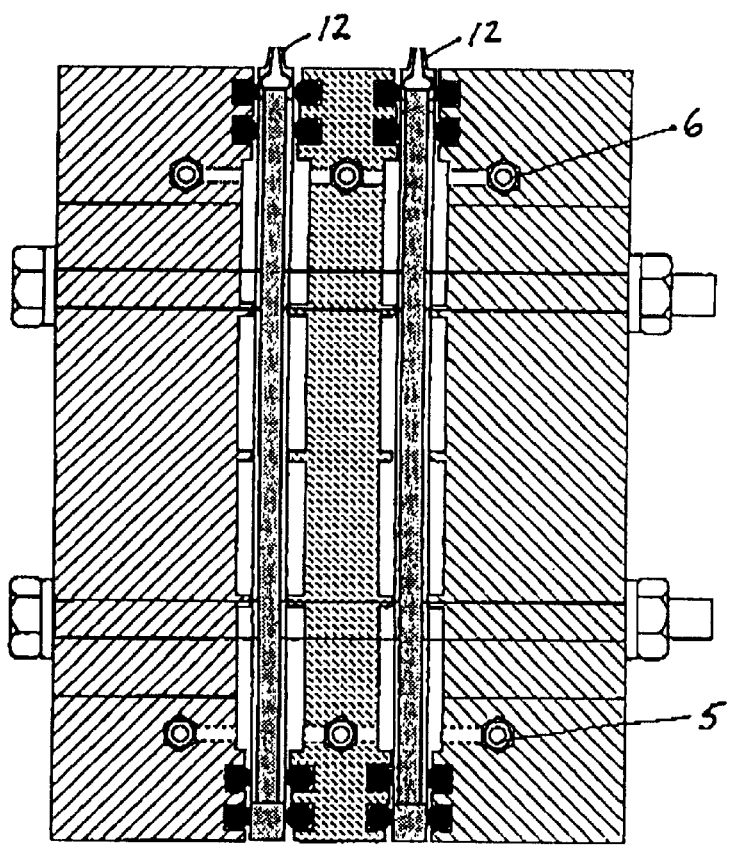
FIG. 12 shows the same configuration as FIG. 11 in section.

FIGS. 11 and 12 show different views of a device including two cells of any type described above in a stacked configuration. For filtration of larger volumes this type of arrangement is very convenient. A large number of cells could be stacked in this way. In this case external manifolds connected to the inlets 5 and outlets 6 as well as the filtrate outlets 12 are distributing and collecting the respective liquids.

Figure 13:
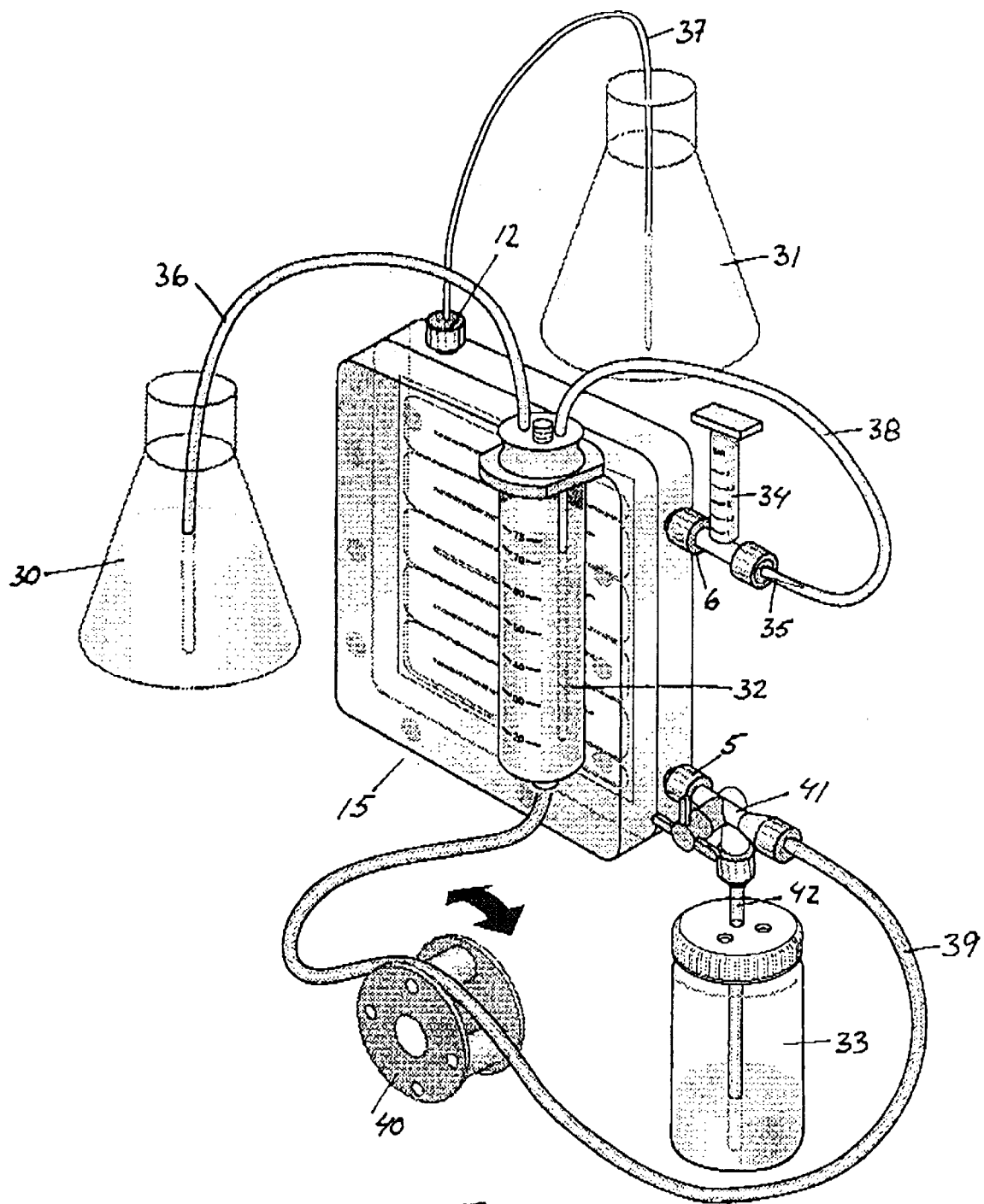
FIG. 13 shows the filtration loop according to the invention.

FIG. 13 shows a filtration loop according to the invention. The filtration cell designated 15 is of the cross flow type. A vessel 30 is provided for the sample solution to be processed. Another vessel 31 is arranged to collect the filtrate and a further vessel 33 is used for concentrate recovery.

A circulation reservoir 32 is shown attached in the particular embodiment to the filtration cell. Of course the reservoir does not have to be physically attached to the filter cell but it is a convenient solution. On the outlet 6 from the cell are connected a pressure gauge 34 and a flow restrictor 35. The flow restrictor is used to create and control the back pressure in the cell. This back pressure is needed to create and maintain the flux of filtrate through the membrane. The appropriate tubings between the different devices include a tube 36 connecting the sample vessel 30 to the recirculation reservoir 32, a tube 37 connecting the filtrate outlet 12 on the filter cell to the filtrate vessel 31, a tube 38 connecting the sample outlet 6 on the cell with the recirculation reservoir 32 and a tube 39 connecting the recirculation reservoir via a peristaltic pump 40 to the sample inlet 5 on the cell. The pump could be of any other appropriate type.

By means of the tube connections a recirculation loop is created including the recirculation reservoir 32, the tube 39, the pump 40 the valve 41, the cell 15 from inlet 5 to outlet 6, the flow restrictor 35 and the tube 38 back to the recirculation reservoir. This loop is created with the view of having a very small recirculation volume and minimise the total length of tubing. The two tubes 36 and 38 entering the recirculation reservoir are sealed air-tight to the reservoir. The volume of this reservoir is chosen to approximately equal the final concentration volume and the cross sectional area of the reservoir is chosen small. The pump sucks liquid from the lower part of the recirculation reservoir. When air is entering the pump and thereby the rest of the loop the concentration has to stop due to foaming and other problems. The means that the concentration can continue to smaller volumes if the recirculation reservoir has a small diameter at least in its lower part.

During the concentration procedure filtrate is permeating through the membrane so that the liquid volume in the loop decreases. This creates an underpressure in the recirculation reservoir which sucks new sample from the sample vessel 30 into the reservoir.

An advantage with this system is that once the user has reached the concentration of interest he can then wash the concentrated solution in a classical diafiltration procedure, if he so wishes, using the same vessel 30 now provided with buffer solution. The setup of the system does not have to be changed.

As can be seen in FIG. 13 the recirculation reservoir is graduated so that the user can all the time read the actual concentration. The volume of the rest of the loop is included in the reading. The accuracy is in the order of one ml.

The inlet 5 to the filtration cell is in this embodiment provided with a three way valve 41 and a branch conduit 42 connected to this valve ends in a concentrate recovery vessel 33. When the user wishes to take out concentration from the loop the pump speed is reduced and a connection to the branch conduit is established through the valve 41. The pump continues to transport liquid through the loop and a portion of the concentrate will "bleed" off from the loop into the vessel 33. No new sample is sucked into the system due to the increased pressure in the reservoir 32.

To empty the system from liquid that has not been pumped out, especially rests of liquid on the filter cell, the system can be pressurised through the tube 36, e.g. by means of a syringe. As the flow path through the pump is blocked the pressure will enter the filter cell at the top through the outlet 6 and drain the cell through the valve 41 into the vessel 33.

When a new concentration of diafiltration cycle is to be started from an empty loop the system has first to be primed. Liquid, e.g. water or sample solution in the case of concentration, and the concentrate in case of diafiltration, is filled into the vessel 33 and the pump is run in the reverse direction i.e. sucking liquid from the vessel 33 and pumping it into the recirculation reservoir. When this has been filled up the process can be started. The valve 41 is switched to the proper position and the pump direction and speed is set.

In FIG. 14 a new pressure gauge 42 is shown. The problems with pressure gauges in this type of small laboratory systems are that they hold up quite some liquid which means that they are not sanitary and they are expensive. Of course there also exist pressure gauges which do not hold up liquid but they are much too expensive for this type of equipment. Furthermore the reading fluctuates with the pressure oscillations in the system due to the pump which makes the reading of most pressure gauges difficult. FIG. 14 shows a very simple and inexpensive pressure gauge 42 which is sufficiently accurate for the purpose and has the further advantage that it does not have any dead volume. A cylindrical housing 46 with a very thin inlet channel 45 at one end comprises a piston 44 which is sealed against the inner wall of the housing by means of a simple O-ring. The piston 44 is biased against the opening of the inlet channel into the housing by means of a spring 43 arranged between the piston and a back plate 47 at the opposite end of the housing. The housing is at least partly transparent so that the position of the piston could be read against a graduation on the cylindrical wall of the housing. Thus, actual pressure is indicated by the displacement of the piston in the housing. The pressure oscillations attenuated by the thin inlet channel 45. In combination with the friction of the O-ring against the inner wall of the housing, makes the reading stable and accurate. When the pump is turned off and the pressure drops the spring 43 will press down the piston 44 and completely empty the gauge. As the inlet channel 45 is very thin a very small volume of liquid will rest.

FIG. 15 shows a T-connection 48 on the outlet 6 from the cell 15 to which the pressure gauge 42 and a flow restrictor 49 are connected. Usually a so called pinch valve is used for creating the back pressure in this type of systems. Such a valve comprises a clamp engaging the flexible tube and by means of a screw, stepping mechanisms or a slideable member the tube is squeezed to restrict the flow in the tube. For these reasons the flow restriction will not have a circular cross section but especially for small openings have the form of a thin slit. Typical restrictions for this type of application should have a cross section of about 0.1–0.2 mm². This means that the flexible tube must be squeezed considerably. Irrespective of the type of adjusting mechanism it will be very difficult to achieve this opening. The mechanisms are not accurate enough at the end of the adjusting interval. In order to get the appropriate back pressure it is therefore also necessary to adjust the pump speed. On top of this the cross section of the opening will not be stable due to the flexible nature of the tube.

A simple restriction in the form of a hole in a plate will not work in this type of application. Material in the sample liquid flow will gradually accumulate around the edges of the hole and finally block the hole.

The invention solves this problem by providing a restrictor in the form of a small conical tube with a predefined opening at the tip. This restrictor will not block due to the flow characteristics in the restrictor. The liquid is gradually accelerated in passing the cone which prevents material to stick to the walls. Very small stable restrictions can easily be realised with this type of device. The only parameter which has to be adjusted to reach the appropriate back pressure is thus the pump speed which greatly simplifies the handling of the equipment. As can be seen in FIG. 15 the restrictor could be mounted as an external easily exchangeable component on the filtration cell. Preferably different sizes of restrictors are provided which makes it easy for the user to chose the appropriate one taking into account the actual process parameters. Additionally the conical form offers a possibility to use the restrictor as a connector for the following tube as shown in the figure.

If a pinch valve is used it has by necessity to be preceded and succeeded by a piece of flexible tube. On the upstream side of the pinch valve the tube has to stand a much higher pressure than on the downstream side. Therefore, the tube has to be chosen based on the parameters directly on the outlet from the cell.

As can be seen in FIG. 15 according to the invention there does not have to be any flexible tube between the outlet 6 and the restrictor. This means that the following tube 38 can chosen to suit the conditions on the downstream side of the restrictor which is very advantageous.

If one and the same type of liquid is to be processed in the same cell, the T-connection 48 including the pressure gauge can be disconnected from the system once the pump speed has been adjusted and noted and the restrictor could then be directly connected to the outlet 6. The pressure gauge would not be further needed to run the system. This would additionally raise the sanitary quality of the loop.

In larger systems other types of flow restrictors are used which are more sophisticated and also more expensive.

In the above we have described the filtration cell and the filtration system in an application on a small laboratory concentration and washing equipment. The inventive idea is, however, easy to implement on large scale industrial production equipment for e.g. the food- and biotechnology industry as well.

What is claimed is:

1. A filtration cell for carrying out a tangential flow filtration of a sample liquid comprising:

at least two blocks;

at least two filtration elements arranged between said blocks;

each said filtration element having an outlet for a filtrate and comprising a sheet of support material for collecting the filtrate, and two generally flat ultrafiltration or microfiltration membranes arranged on either side of the support material in a sandwich construction;

each of the blocks at a side adjacent the membranes being provided with a respective channel for feeding a flow of sample liquid tangentially over the membranes such that each channel is connected to parallel with an inlet for the flow of sample liquid to be filtered and with an outlet for a concentrated solution;

each channel including in its longitudinal direction a number of subsequent flow channel sections separated by transitional zones; each section being associated with a main flow direction; and said channel sections being structured and arranged such that the main flow direction in subsequent flow channel sections changes abruptly when the flow passes a transitional zone.

2. The filtration cell according to claim 1, wherein the main flow direction in subsequent flow channel sections changes by about 70° in each transitional zone.

3. The filtration cell according to claim 1, wherein the main flow direction in subsequent flow channel sections changes by between about 200° and 220° in each transitional zone.

4. A tangential flow filtration system comprising:

a tangential flow filtration cell including a filtration membrane having a feed side and a permeate side; said cell having an inlet and an outlet for guiding a sample flow from the inlet to the outlet tangentially along the surface of the filtration membrane;

said cell being connected in a recirculation loop having a pump;

said outlet comprising a flow restrictor; and said flow restrictor having the form of an external exchangeable cone with a decreasing cross sectional area in the direction of the flow.

5. The tangential flow filtration system according to claim 4, wherein the tangential flow filtration cell has a generally flat filtration membrane; said tangential flow filtration cell being provided with at least one thin tangential flow channel in contact with the feed side of the membrane; the filtrate passing the membrane from the feed side to the permeate side in a flow essentially perpendicular to the sample flow on the feed side; said at least one channel including in its longitudinal direction a number of subsequent channel sections separated by transitional zones; each section being associated with a main flow direction; said channel sections being structured and arranged such that the main flow direction in subsequent flow channel sections changes abruptly when the flow passes a transitional zone; and a width of said at least one channel progressively increases in the direction of flow.

* * * * *